(12) United States Patent
Chen

(10) Patent No.: US 7,482,122 B1
(45) Date of Patent: Jan. 27, 2009

(54) METHOD OF SIGNAL ENHANCEMENT FOR MEASUREMENT OF NUCLEIC ACID SEQUENCES

(76) Inventor: Hai Xing Chen, 700 Bay Street, PH B, Toronto, Ontario (CA) M5G 1Z6

(*) Notice: Subject to any disclaimer, the term of this patent is extended or adjusted under 35 U.S.C. 154(b) by 55 days.

(21) Appl. No.: 11/255,350

(22) Filed: Oct. 19, 2005

Related U.S. Application Data

(60) Provisional application No. 60/620,091, filed on Oct. 19, 2004.

(51) Int. Cl.
*C12Q 1/68* (2006.01)
(52) U.S. Cl. .......................................... 435/6
(58) Field of Classification Search .................. None
See application file for complete search history.

(56) References Cited

U.S. PATENT DOCUMENTS

| | | | | |
|---|---|---|---|---|
| 5,503,979 A | * | 4/1996 | Kramer et al. ............... | 435/6 |
| 5,681,697 A | * | 10/1997 | Urdea et al. ................. | 435/6 |
| 5,712,383 A | * | 1/1998 | Sheridan et al. ............. | 536/24.3 |
| 6,531,286 B2 | * | 3/2003 | Jayasena et al. ............. | 435/6 |

* cited by examiner

*Primary Examiner*—Gary Benzion
*Assistant Examiner*—Suchira Pande
(74) *Attorney, Agent, or Firm*—Yi Li

(57) ABSTRACT

A method of enhancing detection signal for measurement of nucleic acid sequences includes providing a T- or L-primary probe having a target-binding segment and an enhancer linker segment; and hybridizing the primary probe with a target sequence of interest; providing a first enhancement probe having a first annealing segment complementary to the enhancer linker segment, a second annealing segment and a chemical label; hybridizing the first enhancement probe to the primary probe; providing a second enhancement probe having a first annealing segment complementary to the second annealing segment of the first enhancement probe, a second annealing segment complementary to the first annealing segment of the first enhancement probe, and the same chemical label; hybridizing the first and second enhancement probes, thereby multiple first and second enhancement probes annealing with each other forming a staggered chain extending from the primary probe; and detecting the chemical labels in the final complex.

9 Claims, 9 Drawing Sheets

Enhancement probe hybridization pattern.

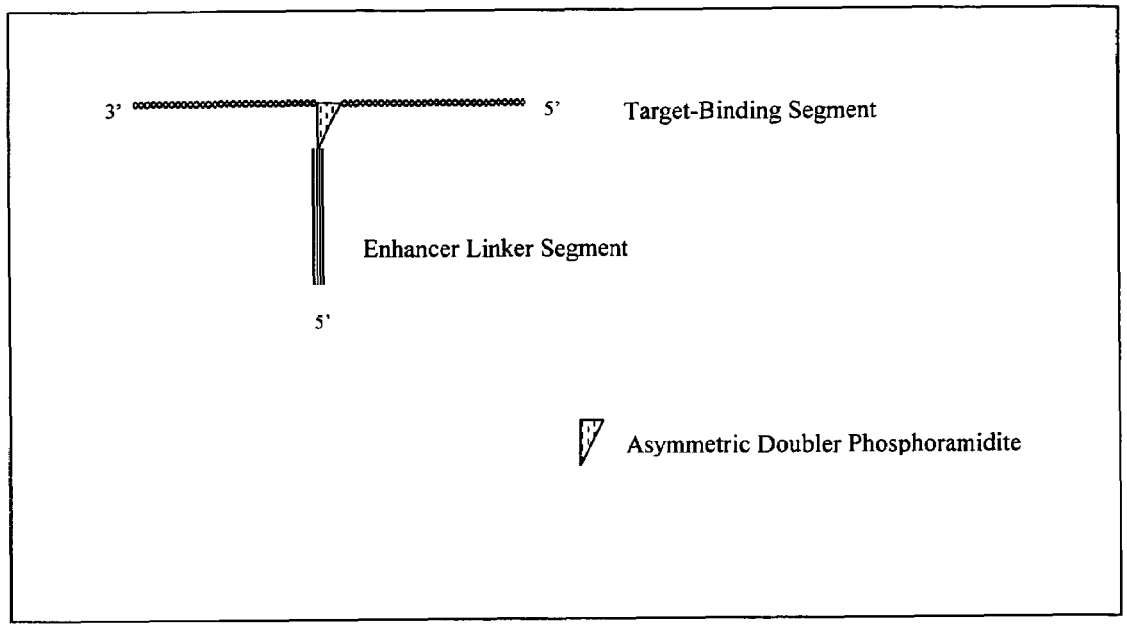
Fig. 1a T-Primary probe structure

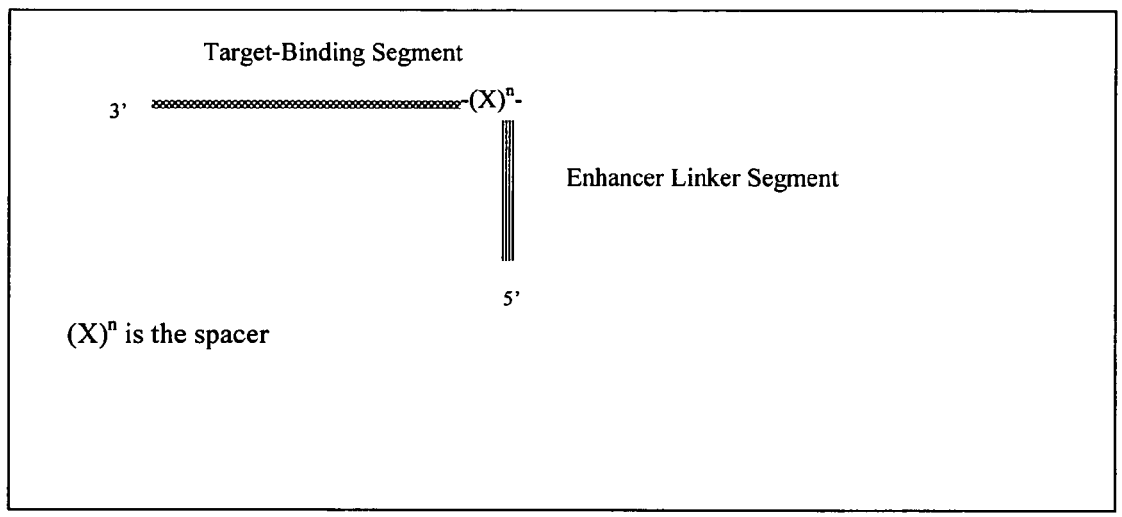
Fig. 1b L-Primary probe structure

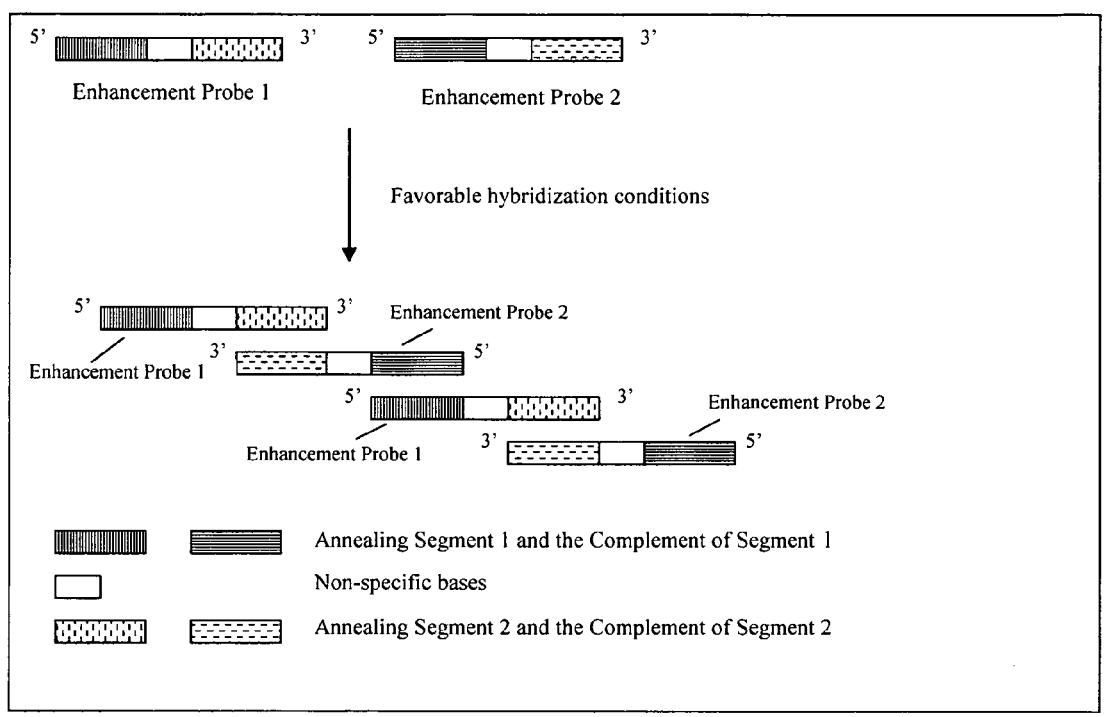
Fig. 2 Enhancement probe hybridization pattern.

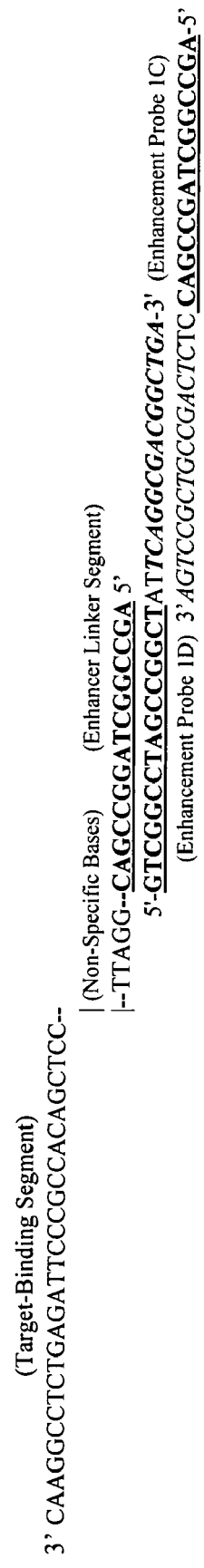
Fig. 3a Hybridization between a T-Primary Probe and a pair of enhancement probes
Fig. 3b Hybridization between a L-Primary Probe and a pair of enhancement probes Fig. 4. Synthesis of T-Primary Probe
(a) The target-binding segment sequence synthesized
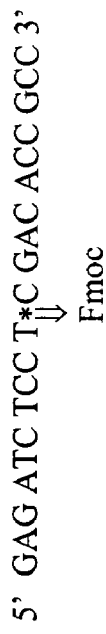
5' GAG ATC TCC T*C GAC ACC GCC 3'
           ⇩
          Fmoc
(b) The obtained T-primary probe with the enhancer linker sequence synthesized
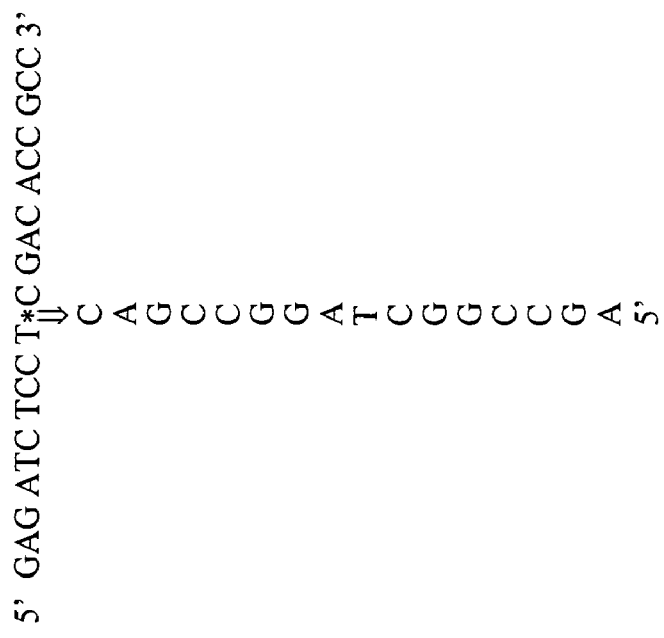
5' GAG ATC TCC T*C GAC ACC GCC 3'

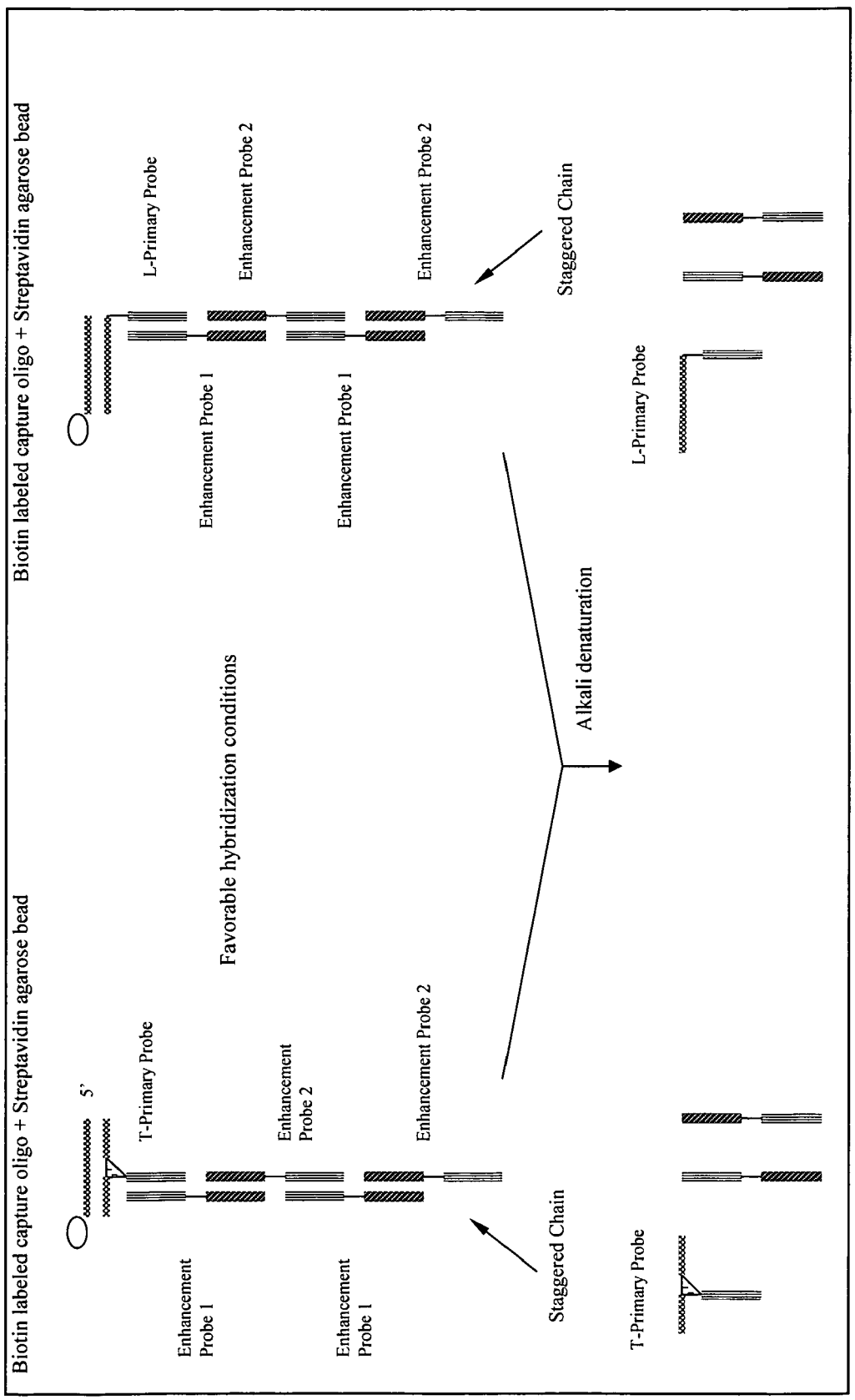
Fig. 5 Schematic illustration of the process for testing enhancement probe hybridization described in Example 4

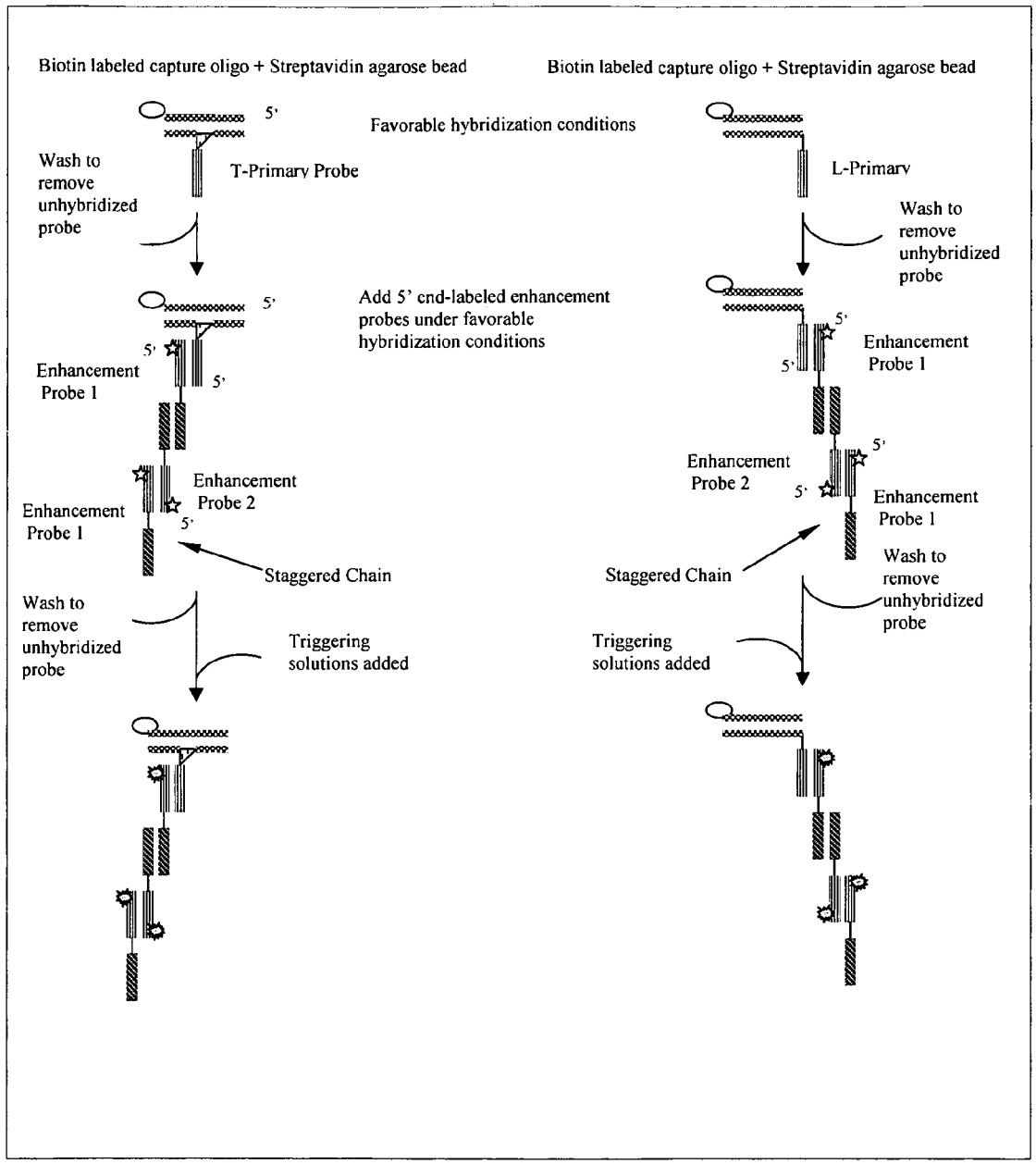
Fig. 6 Schematic illustration of the process of analysis of nucleic acid in a sample using a T- or L- primary probe and a pair of enhancement probes

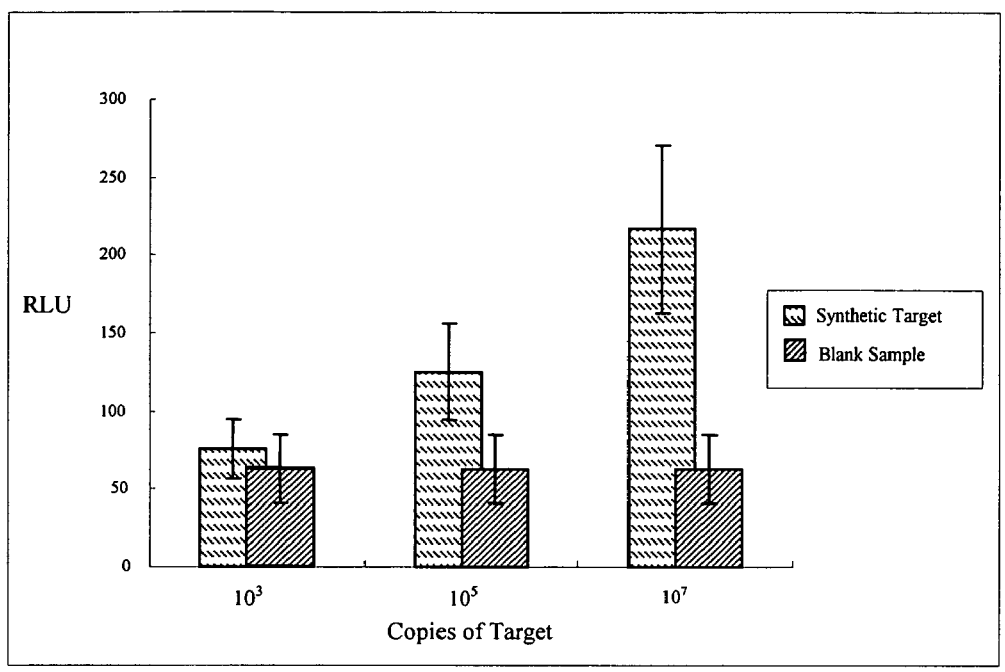
Fig. 7a Relative light units (RLU) vs. copies of the target, obtained using AE-labeled linear probe.

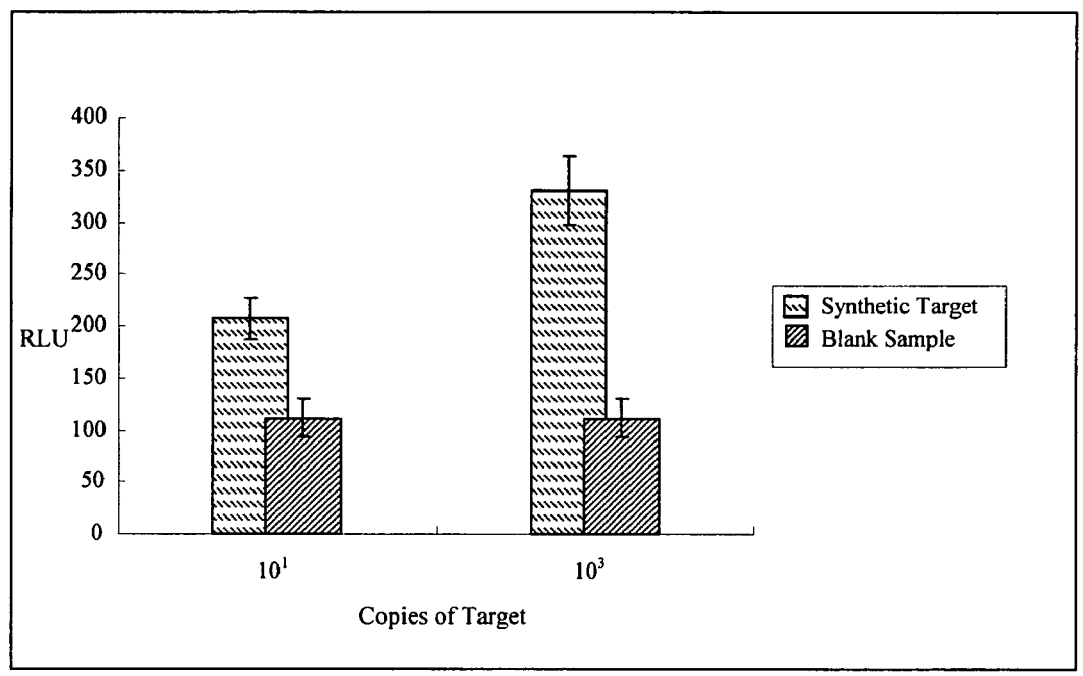
Fig. 7b Relative light units (RLU) vs. copies of the target, obtained using T-primary probe with enhancement probes 1C and 1D shown in Table 1.

US 7,482,122 B1

METHOD OF SIGNAL ENHANCEMENT FOR MEASUREMENT OF NUCLEIC ACID SEQUENCES

CROSS REFERENCE TO RELATED APPLICATION

This application claims the benefit under 35 USC 119 (e) of the provisional patent application Ser. No. 60/620,091, filed on Oct. 19, 2004, which is herein incorporated by reference in its entirety.

FIELD OF THE INVENTION

The present invention relates to a method of signal enhancement for measurement of a nucleic acid sequence. More specifically, the method uses a combination of a primary probe having an enhancer linker segment and a pair of complementary enhancement probes for increasing signals for effective measurement of low concentration of nucleic acids in a sample.

BACKGROUND OF THE INVENTION

In molecular diagnosis, the target DNA or RNA sequences in a sample are frequently at very low concentrations, which can be around or below the detection limit of available clinical diagnostic methods. This renders the analysis of these samples unreliable, or impossible. Currently, the detection limit of available methods is at the level about $10^5$ copies of the target sequence in a sample. However, a concentration of certain DNA and RNA sequences in a sample substantially below this level can be clinically significant.

The well-known PCR method was developed for solving this specific problem. In general, PCR based assays increase the concentration of a target sequence from its original concentration in the sample, and subsequently measure the target sequence after the amplification. However, PCR based assays have complicated and lengthy sample preparation process, and require highly trained laboratory personals. The PCR based assays typically require up to 24 hours to obtain the analysis results.

It is desirable to be able to enhance the detectable signals of low concentration nucleic acids and to reduce the current detection limits without amplifying the concentration of the target sequence.

BRIEF DESCRIPTION OF THE DRAWINGS

FIG. 1a illustrates the structure of a T-primary probe.

FIG. 1b illustrates the structure of a L-primary probe.

FIG. 2 illustrates the hybridization pattern of enhancement probes.

FIG. 3a illustrates hybridization pattern between a T-primary probe and a pair of enhancement probes.

FIG. 3b illustrates hybridization pattern between a L-primary probe and a pair of enhancement probes.

FIG. 4 illustrates a two step synthesis of a T-primary probe.

FIG. 5 is a schematic illustration of the process for testing enhancement probe hybridization described in Example 4.

FIG. 6 is a schematic illustration of the process of analysis of nucleic acid in a sample using a T- or L-primary probe and a pair of enhancement probes of the present invention.

FIG. 7a shows the test results obtained using an AE-labeled linear probe.

FIG. 7b shows the test results obtained using a T-primary probe with a pair of enhancement probes of the present invention.

SUMMARY OF THE INVENTION

In one aspect, the present invention is directed to a method of enhancing detection signal for measurement of nucleic acid sequences. The method comprises the steps of: providing a solid capture support comprising an immobilized capture sequence complementary to a capture-binding segment of a single strand nucleic acid target sequence of interest; hybridizing the capture-binding segment of the target sequence from a sample with the capture support to form a target-capture complex; removing unhybridized target sequence; providing a T- or L-primary probe comprising a target-binding segment and an enhancer linker segment; and hybridizing the target-binding segment of the primary probe with a probe-binding segment of the target sequence to form a capture-target-primary probe complex; removing unhybridized T- or L-primary probe; providing a first enhancement probe comprising a first annealing segment complementary to the enhancer linker segment of the primary probe, a second annealing segment and a chemical label; and hybridizing the first annealing segment of the first enhancement probe with the enhancer linker segment of the primary probe; providing a second enhancement probe comprising a first annealing segment complementary to the second annealing segment of the first enhancement probe, a second annealing segment complementary to the first annealing segment of the first enhancement probe, and the chemical label; and hybridizing the second enhancement probe with the first enhancement probe, thereby multiple the first and second enhancement probes annealing with each other forming a staggered chain extending from the enhancer linker segment of the primary probe, and forming a final complex containing multiple the chemical labels; removing unhybridized the first and second enhancement probes; detecting the chemical labels in the final complex; and determining the presence of the target sequence in the sample.

The chemical label is a chemiluminescence or a fluorescence molecule. The method can further comprise triggering chemical labels using a triggering solution prior to detecting the chemical labels.

In a further aspect, the present invention is directed to a diagnostic kit for measurement of nucleic acid sequences. The diagnostic kit comprises a primary probe formed of a first single strand nuclei acid sequence comprising a target-binding segment complementary to a segment of a nucleic acid target sequence of interest and an enhancer linker segment; a first enhancement probe formed of a second single strand nuclei acid sequence comprising a first annealing segment complementary to the enhancer linker segment of the primary probe, a second annealing segment and a chemical label; and a second enhancement probe formed of a third single strand nuclei acid sequence comprising a first annealing segment complementary to the second annealing segment of the first enhancement probe, a second annealing segment and the chemical label.

In one embodiment, the primary probe is a T-primary probe having an asymmetric doubler phosphoramidite connecting between the target-binding segment and the enhancer linker segment. In another embodiment, the primary probe is a L-primary probe having a spacer between the target-binding segment and the enhancer linker segment.

The first and second enhancement probes can also comprise a spacer between the first annealing segments and the second annealing segments. The chemical label is a chemiluminescence or a fluorescence molecule.

The diagnostic kit can further comprise a capture support comprising a capture nucleic acid sequence complementary to a segment of a target nucleic acid sequence to be detected. The diagnostic kit can also comprise one or more hybridization solutions. In one embodiment, the hybridization solution is a guanidinium thiocyanate solution.

DETAILED DESCRIPTION OF THE INVENTION

In one aspect, the present invention provides a diagnostic kit for use in the analysis of nucleic acid sequences to amplify detectable signals of the nucleic acid sequence.

The kit comprises a primary probe and a pair of enhancement probes. The primary probe comprises two segments. The first segment is a target-binding segment containing a nucleic acid sequence that is complementary to a segment of the target sequence of interest. The second segment is a nucleic acid sequence that is complementary to one segment of an enhancement probe. Hence, the second segment is referred to as enhancer linker segment hereinafter. The term "target sequence" used herein refers to a nucleic acid sequence to be detected, which can be a natural nucleic acid sequence in a biological sample, or a synthetic nucleic acid sequence. For the purpose of detection, the target sequence has a capture-binding segment which can bind to a capture sequence, and a probe-binding segment which can bind to a complementary probe used for the detection.

In one embodiment, the primary probe has a T-structure, as shown in FIG. 1a. The target-binding segment is a linear DNA sequence separated by an asymmetric doubler phosphoramidite. The enhancer linker segment is connected to one site of the doubler phosphoramidite.

Alternatively, the primary probe can also have a L-structure, as shown in FIG. 1b. The L-primary probe is a linear DNA sequence having a number of non-specific nucleotides, which form a spacer, separating the target-binding segment from the enhancer linker segment.

With either primary probe structure, upon hybridization of the target-bind segment to the probe-binding segment of a target sequence, the enhancer linker segment remains as a free port for attachment of the enhancement probes.

The pair of enhancement probes of the present invention are two linear DNA oligonucleotides. Each enhancement probe comprises a first annealing segment, a second annealing segment, and a spacer between the two segments, as shown in FIG. 2. The first annealing segment of the first enhancement probe within the pair is complementary to the enhancer linker segment sequence of the primary probe, which hybridizes to the enhancer linker segment under a hybridization condition. On the other hand, within the pair, the first annealing segment of the second enhancement probe is complementary to the second annealing segment of the first enhancement probe, and the second annealing segment of the second enhancement probe is complementary to the first annealing segment of the first enhancement probe. Under a hybridization condition, the first and the second enhancement probes form a staggered chain linking a plurality of enhancement probes to the primary probe, as shown in FIGS. 5 and 6. When the paired enhancement probes are labeled with detectable labels, the numbers of detectable labels attached to one target sequence, via one primary probe, can be increased significantly.

The spacer does not bind to the target sequence, the primary probe or the enhancement probes. Suitable examples of the spacers include a number of non-specific nucleotides, as shown in Table 1, and a spacer phosphoramidite, or other suitable spacers known in the art.

In a preferred embodiment, the sequence of the enhancer linker segment of the primary probe is the same as the sequence of the second annealing segment of the second enhancement probe.

In a further embodiment, the kit can further comprise a capture support which comprises an immobilized capture sequence complementary to a capture-binding segment of the target sequence to be analyzed, as described hereinafter in detail. Additionally, the kit can further comprise reagents used for the analysis of the target sequences, such as hybridization solutions and wash solutions.

The structures and syntheses of T- and L-primary probes and enhancement probes are described in detail hereinafter.

Enhancement Probes

The enhancement probes are a pair of linear DNA oligonucleotides, both have similar sequence length. As illustrated in FIG. 2, in one pair, both enhancement probe 1 and enhancement probe 2 comprise three sections (5' to 3'): (1) annealing segment 1 or the complement of segment 1; (2) non-specific nucleotides, or bases; and (3) annealing segment 2 or the complement of segment 2. It is noted that as an abbreviation, oligonucleotide is also commonly referred to as oligo.

The non-specific bases are short strings of random bases inserted to separate the two annealing segments. However, these non-specific bases within enhancement probe 1 are not complementary to the non-specific bases of enhancement probe 2. These bases remain single stranded after the annealing of the two enhancement probes because of the staggered pattern formed. The length of the pair of DNA oligonucleotides can be variable depending on the specifications of the application that will be used. Prior to synthesis of the oligonucleotide pair, each enhancement probe sequence was put through NCBI (National Center for Biotechnology Information) BLASTN 2.2.6 to check if there were any significant matches in the database. This was required to prevent potential non-specific binding of an enhancement probe to a nucleic acid region (viral, bacterial, human) other than their designated complementary sequences designed into the instant enhance signal amplification method.

Synthesis of Enhancement Probe

Each of the enhancement probes were synthesized by standard procedures on a commercially available oligonucleotide synthesizer (ABI DNA Synthesizer, Forest City, Calif.). Table 1 shows a number of pairs of enhancement probes synthesized, which have different lengths. The enhancement probes were then chemically linked to a chemiluminescent molecule. In a preferred embodiment, Acridinium $C_2$ NHS ester (4-(2-succinimidyl-oxycarbonylethyl) phenyl-10-acridinium-9-carboxylate trifluoromethyl sulfonate), from Assay Designs (Ann Arbour, Mich.), was used as the label. For short, acridinium $C_2$ NHS ester is herein also referred to as acridinium ester, or AE. The details of synthesis are described in Example 3 hereinafter.

TABLE 1

| Synthesis of Enhancement Probe Sequences | | |
|---|---|---|
| Enhancement Probe (EP) | Annealing Segment 1 (5'-3') | Non-specific bases (5'-3') | Annealing Segment 2 (5'-3') |
| EP 1 (57 bases) | ACTTGCGTCGGCC TAGCCGGCT (SEQ ID NO:1) | ATATATTA (SEQ ID NO:2) | TCAGGCGACGGCT GAATCGGAAAGGC C (SEQ ID NO: 3) |

TABLE 1-continued

Synthesis of Enhancement Probe Sequences

| Enhancement Probe (EP) | Annealing Segment 1 (5'-3') | Non-specific bases (5'-3') | Annealing Segment 2 (5'-3') |
|---|---|---|---|
| EP 2 (57 bases) | AGCCGGCTAGGCC GACGCAAGT (SEQ ID NO:4) | TCCCTACG (SEQ ID NO:5) | GGCCTTTCCGATT CAGCCGTCGCCTG A (SEQ ID NO: 6) |
| EP 1A (45 bases) | TGCGTCGGCCTAG AT CCGGCT (SEQ ID NO:7) | | TCAGGCGACGGCT GAATCGGAAAG (SEQ ID NO:8) |
| EP 1B (45 bases) | AGCCGGCTAGGCC TC GACGCA (SEQ ID NO:9) | | CTTTCCGATTCAG CCGTCGCTGA (SEQ ID NO:10) |
| EP 1C (33 bases) | GTCGGCCTAGCCG AT GCT (SEQ ID NO:11) | | TCAGGCGACGGCT GA (SEQ ID NO:12) |
| EP 1D (33 bases) | AGCCGGCTAGGCC TC GAC (SEQ ID NO:13) | | TCAGCCGTCGCCT GA (SEQ ID NO:14) |

Primary Probe

As described previously, the primary probe comprises two segments. The first segment is a target-binding segment, which has the sequence that can hybridize to the probe-binding segment of the target sequence. The second segment is the enhancer linker segment which is a sequence that can hybridize to one segment of the enhancement probe. The sequence of the second segment is complementary to the sequence of annealing segment 1 of either one of the enhancement probes. FIG. 3b illustrates an exemplary structure of a T-primary probe, annealing of enhancement probe 1C with the T-primary probe, and annealing of enhancement probe 1D with enhancement probe 1C.

T-Primary Probe

Synthesis of the T-primary probe was based on the method taught by M. S. Shchepinov using an asymmetric doubler phosphoramidite, Glen Research, Vol. 12, No. 1, November 1999, which is herein incorporated by reference in its entirety. The doubler phosphoramidite has two primary hydroxyl groups protected with DMT (4,4'-dimethoxytrityl) and Fmoc (N-alpha-(9-fluorenyl-methyloxycarbonyl)). Once the doubler phosphoramidite is incorporated into the target-binding segment sequence, the remaining target-binding segment sequence is built upon the DMT-protected arm. After the synthesis of the target-binding segment is completed, the Fmoc arm is deprotected and an enhancer linker segment sequence can be synthesized. In other words, T-primary probe can be synthesized in two steps. The first step incorporates a doubler phorporamidite into the target-binding segment sequence. The second step adds on the enhancer linker sequence at the doubler phosphoramidite site. This results in a branched oligonucleotides with two 5' ends.

Several T-primary probes have been synthesized with the doubler phosphoramidite incorporated into different positions of the target-binding segment sequence. More specifically, one has the doubler phosphoramidite in the middle of a 20 base target-binding segment sequence; one has the doubler phosphoramidite positioned after 15 bases of a 20 base target-binding segment; and one has the doubler phosphoramidite positioned after 20 bases of a 23 base target-binding segment, as shown in Table 2.

L-Primary Probe

In addition to the T-primary probe structure, other primary probe structures can be used to create branched probe structure desired for the purpose of the present invention. Long, linear oligonucleotides were synthesized, as shown in Table 2. These linear primary probes comprise a target-binding segment sequence, an enhancer linker segment sequence and a spacer which separate the target-binding segment sequence and the enhancer linker segment sequence. As shown in FIG. 1b, the enhancer linker segment in the L-primary probe is like a tail, freely suspending after the target-binding segment, because neither the enhancer linker segment sequence, nor the spacer, hybridizes to the target sequence. Hence, the enhancer linker segment sequence in the L-primary probe is also referred to as a tail. As described above for the enhancement probes, the spacer in the L-primary probe can be a number of non-specific nucleotides, as shown in Table 2, a spacer phosphoramidite, or other suitable spacers known in the art.

The syntheses of these primary probes were completed using a standard protocol for linear oligonucleotide synthesis on the ABI DNA Synthesizer. Furthermore, because of the linear nature of this primary probe, cartridge purification was performed to obtain full length sequence.

The design of the enhancer linker segment sequence is critical. If the enhancer linker segment sequence hybridizes anywhere along the target sequence, which are in close proximity to the tail after the hybridization of the target-binding segment, the enhancer linker segment sequence will no longer be a free tail. This can result in substantial decrease of the probability for the enhancement probes to hybridize to the enhancer linker segment.

TABLE 2

T- and L- Primary Probe Sequences

| Probe | Branch Point | Target-binding segment sequence (5'-3') | Enhancer linker segment Sequence (5'-3') |
|---|---|---|---|
| T- Primary Probe 1 | 10/10 | "GAGATCTCCT" (SEQ ID NO:15) X "CGACACCGCC" (SEQ ID NO:16) | AGCCGGCTAGGCCG AC (SEQ ID NO: 17) |
| T- Primary Probe 2 | 15/5 | "GAGATCTCCTCGA CA" (SEQ ID NO: 18) X "CCGCC" (SEQ ID NO:19) | AGCCGGCTAGGCCG AC (SEQ ID NO: 17) |
| T- Primary Probe 3 | 20/3 | "GAGATCTCCTCGAC ACCGCC" (SEQ ID NO:20) X-"TCT" (SEQ ID NO:21) | AGCCGGCTAGGCCG AC (SEQ ID NO: 17) |

| Probe | Length | Sequence (5'-3') |
|---|---|---|
| L- Primary Probe 1 | 41 | AGCCGGCTAGGCCGACGGATT"GAGATCTCCT CGACACCGCC" (SEQ ID NO:22) |
| L- Primary Probe 2 | 51 | AGCCGGCTAGGCCGACGGATT"CCTCGACACC GCCCTTAGAGTCTCCGGAAC" (SEQ ID NO:23) |

TABLE 2-continued

T- and L- Primary Probe Sequences

| L- Primary Probe 3 | 41 | AGCCGGCTAGGCCGACGGATT"GCCCTTAGAG TCTCCGGAAC" (SEQ ID NO:24) |
|---|---|---|

Note:
Target-binding segment sequence is in quote "", and enhancer liner segment is italicized.

In a further aspect, the present invention provides a method of enhancing or amplifying detectable signals to facilitate measurement of nucleic acid sequences at a low concentration, using the primary probes and the paired enhancement probes described above.

In one embodiment, the method comprises following steps:

(1) providing a solid capture support in a reaction vessel, the capture support comprising an immobilized capture sequence complementary to a capture-binding segment of a single strand nucleic acid target sequence of interest;

(2) adding a first hybridization solution in the reaction vessel;

(3) adding a sample containing a single strand nucleic acid target sequence to be detected and hybridizing the capture-binding segment of the target sequence to the capture support in the first hybridization solution to form a capture-target complex;

(4) washing the capture support to remove unhybridized target sequence;

(5) adding a second hybridization solution in the reaction vessel;

(6) adding a T- or L-primary probe comprising a target-binding segment and an enhancer linker segment; and hybridizing the target-binding segment of the primary probe to a probe-binding segment of the target sequence in the second hybridization solution to form a capture-target-primary probe complex;

(7) washing the capture support carrying the capture-target-primary probe complex to remove unhybridized T- or L-primary probe;

(8) adding a third hybridization solution in the reaction vessel;

(9) adding a first enhancement probe comprising a first annealing segment complementary to the enhancer linker segment of the primary probe, a second annealing segment and a chemical label; and hybridizing the first annealing segment of the first enhancement probe with the enhancer linker segment of the primary probe in the third hybridization solution;

(10) adding a second enhancement probe comprising a first annealing segment complementary to the second annealing segment of the first enhancement probe, a second annealing segment complementary to the first annealing segment of the first enhancement probe and the same chemical label; and hybridizing the second enhancement probe with the first enhancement probe, thereby multiple first and second enhancement probes annealing with each other forming a staggered chain extending from the enhancer linker segment of the primary probe, and forming a final complex which contains multiple the same chemical labels;

(11) washing the capture support carrying the final complex to remove unhybridized first and second enhancement probes;

(12) detecting the chemical labels in the final complex; and

(13) determining the presence of the target sequence in the sample.

Preferably, the chemical label is a chemiluminescent or fluorescent molecule and the measurement in step (12) is a chemiluminescence or fluorescence measurement. When the chemical label is a chemiluminescent molecule, the method further comprises one more step of adding a chemiluminescent triggering solution prior to detecting the chemical labels in the final complex. The instant method is more fully illustrated in Example 5.

The term "reaction vessel" used herein refers to a device which can be used to perform the hybridization reactions and the washing steps, which includes, but is not limited to, test tube, container, column, and filter.

The following examples are illustrative of the invention and are in no way to be interpreted as limiting the scope of the invention, as defined in the claims.

EXAMPLE 1

Preparation of a T-Primary Probe

A T-primary probe was synthesized using an asymmetric doubler phosphoramidite (Glen Research, Sterling, Va.) which contains two primary hydroxy groups protected with DMT (4,4'-dimethoxytrityl) and Fmoc (N-alpha-(9-fluorenylmethyloxycarbonyl)). The T-primary probe synthesized is illustrated in FIG. 4. Synthesis was completed on Millipore Expedite™ Nucleic Acid Synthesis System. All reagents used with this system were purchased from Applied Biosystems (Forest City, Calif.).

First, the target-binding segment sequence was programmed into the synthesizer, from 5' to 3', as GAG ATC TCC T*C GAC ACC GCC (SEQ ID NO: 15). The symbol "*" shown in FIG. 4 represents the position where the asymmetric doubler phosphoramidite was incorporated. A 0.2 μmole column was filled with 1000 Å CPG (Controlled Pore Glass), this size was used to provide more room for the T-primary probe to grow. The standard coupling program was modified to include a 15 minute wait step after the incorporation of the asymmetric doubler phosphoramidite. After the addition of the asymmetric doubler phosphoramidite, synthesis of the target-binding segment sequence continues from the DMT-protected arm only.

Upon completing synthesis of the target-binding segment sequence, also referred to as the first strand, the DMT-protected arm of the target-binding segment sequence was capped using the manual modes on the synthesizer. Capping stops the addition of any other bases to this arm during the synthesis of the enhancer linker segment sequence. Columns were first primed with an acetonitrile wash. A 1:1 mixture of Capping Reagent A and Capping Reagent B was primed twice through the column. After 20 minutes, the columns were again primed with the same reagent mixture followed by a 1 minute wait. The column was then washed at least three times with the acetonitrile wash.

Next, the Fmoc protection from the asymmetric double phosphoramidite was removed. This exposed OH group on this arm and it was from this arm that the enhancer linker segment sequence was synthesized. The dried CPG were carefully transferred from the column to a clean 1.5 ml screw cap tube. The empty column was cleaned completely and kept aside for later use. A solution of 20% piperidine in DMF (N,N-dimethylformamide), both purchased from Sigma Aldrich Oakville, Ontario, Canada), was prepared. To the screw cap tube, 1 ml of the 20% piperidine/DMF was added, and left at room temperature for 10 minutes, occasionally resuspending CPG in the solution. CPG were spun for 1 minute at maximum speed in bench top microcentrifuge. Solution was carefully removed leaving CPG at bottom of the tube. This step was repeated one more time. CPG were then washed five times in 1 ml DMF, spinning down and removing solution after each rinse. The CPG were then washed 4 times in 1 ml acetonitrile wash, spinning down and removing solution after each rinse. CPG were allowed to dry completely in tubes.

The dry CPG were transferred back to column and put back onto the synthesizer. The enhancer linker segment sequence was then entered into the synthesizer, 5' to 3', AGC CGG CTA GGC CGA C (SEQ ID NO: 17). This sequence was synthesized following the standard 0.2 μmole scale DNA synthesis program. After the enhancer linker segment sequence was added, the complete T-primary probe was cleaved and deprotected following standard DNA synthesis methods.

EXAMPLE 2

Hybridization of the T- or L-Primary Probe

The hybridization of the T-primary probe or L-primary probe, synthesized in Example 1, directly to a capture support was tested.

The capture support was prepared. Streptavidin agarose beads (Molecular Probes Eugene, Oreg.) were linked to a biotin-modified capture oligonucleotide. The capture oligonucleotide had a sequence complementary to the target-binding segment of a T-primary probe. The immobilization of the biotin-modified capture oligonucleotide to the streptavidin agarose beads was completed using a standard method in a buffer containing at least 1.0 M NaCl. It is noted that the capture support can also be prepared using a membrane.

A reaction medium was prepared containing a 10× annealing buffer, water and the capture support described above. The annealing buffer contains 100 μm Tris-HCl, 1.0 M NaCl and 10 mM EDTA. To the reaction medium, either a T-primary probe or a L-primary probe was added to form hybridization mixtures. The hybridization mixtures were tested at different hybridization times and temperatures. The hybridization mixtures were then centrifuged and the capture support was washed three times with a 10 mM Tris-HCl buffer solution to remove any unhybridized probe.

The capture support, or agarose beads, was then subject to alkali denaturation with 2N NaOH to release the hybridized probe from the beads. The denaturant was then neutralized with 2M HCl and an aliquot was run on a 2% agarose gel alongside an aliquot of the reaction medium and of the final wash as the background control. The intensity of the band of the denaturant was observed to determine whether the primary probe hybridized to the capture oligonucleotide.

Results of these experiments showed that the T-primary probes had only slightly lower hybridization yields when compared to the linear probe whose sequence was not interrupted by the doubler phosphoramidite as the T-primary probe sequences were.

EXAMPLE 3

Labeling of Enhancement Probe

The enhancement probes were synthesized with the addition of a 5'-Amino-Modifier C6-TFA (Glen Research, Sterling, Va.). The modified oligonucleotides were then linked to acridinium $C_2$ NHS ester (4-(2-succinimidyl-oxycarbonyl-ethyl) phenyl-10-acridinium-9-carboxylate trifluoromethyl sulfonate) purchased from Assay Designs (Ann Arbour, Mich.).

A 15-25 mM stock solution of the acridinium $C_2$ NHS ester (I) was prepared in DMSO. In a typical experiment, the desired amount of enhancement probe (II) (0.2-0.3 μmol) was dissolved in 200 μl of freshly prepared 0.05M $NaHCO_3$ (pH 8), and 0.30-0.45 μmol of acridinium $C_2$ NHS ester in 20-30 μl of DMSO was added. The mixture was vortexed and left at room temperature. In 30 minutes, an additional portion of 0.30-0.45 μmol of the acridinium $C_2$ NHS ester DMSO solution was added, the mixture was vortexed and left at room temperature for additional 30 minutes. The unreacted label was quenched using a 5-fold excess of lysine.

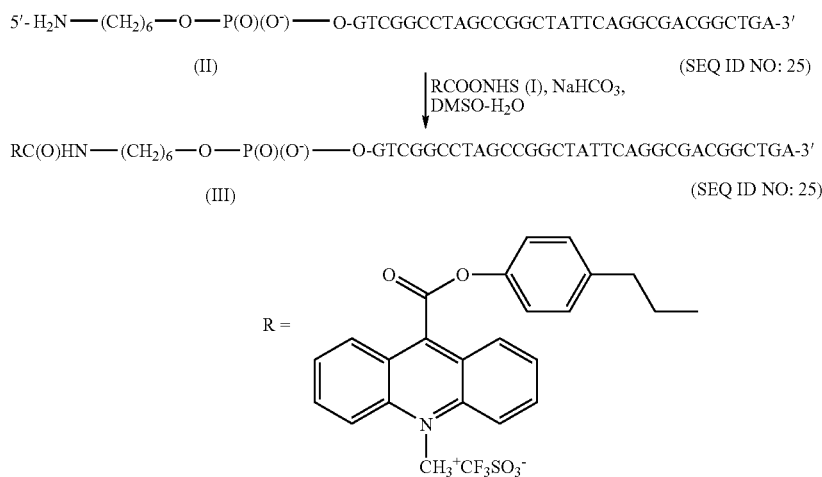

The acridinium ester-labeled probe (III) was then purified using a reverse-phase HPLC. A Delta-Pak C4 3.9×150 mm column was used (Waters, Mississaugua, ON). The separation was achieved using a linear gradient from 0 to 50% of acetonitrile in water in 30 minutes at a flow rate of 2.0 mL/min; absorbance was monitored at UV 260 nm. The main chemiluminescent peak with retention time of 9.5-10.0 min was identified. The mixture was directly injected onto the column (2×50%), the desired fraction was collected and lyophilized. The lyophilized probe was dissolved in water and purified once more in the same conditions. Molar amount of the labelled probe was determined by injecting of a known aliquot onto HPLC in the conditions described above.

EXAMPLE 4

Hybridization of Enhancement Probe to T- or L-Primary Probe

To determine whether the enhancement probes hybridize to the enhancer linker segment extended from the primary probes, the following experiments were performed. The T- and L-primary probes used are listed in Table 2. The capture support was prepared as described in Example 1. The hybridization was determined with two different methods.

In the first method, non-labeled enhancement probes were used. Three hybridization mixtures were prepared, each contained a capture oligonucleotide bound to agarose beads, and a 10× annealing buffer and a T or L-primary probe. As described previously in Example 2, the capture oligonucleotide contained a sequence complementary to the target-binding segment of the T or L-primary probe. To the first hybridization mixtures the enhancement probe containing the sequence segment complementary to the enhancer linker segment was added. To the second hybridization mixtures, a pair of complementary enhancement probes were added. To the third hybridization mixtures, no enhancement probe was added. These hybridization mixtures were incubated at 60° C. for at least 45 minutes. The hybridization reaction is illustrated in FIG. 5.

The hybridization mixtures were then centrifuged and the agarose beads were washed three times with a 10 mM Tris-HCl buffer solution to remove unhybridized primary probe and enhancement probes. The agarose beads were then subject to alkali denaturation with 2N NaOH to release the hybridized primary and enhancement probes from the beads. The denaturant was then neutralized with 2M HCl and an aliquot was run on a 2% agarose gel alongside an aliquot of the original reaction medium (without the primary probe) and of the final wash. To evaluate whether hybridization occurred, the intensity and size of the bands were examined. It was found that the intensities of the bands from the first and the second hybridization mixtures were greater than that from the third hybridization mixture. In other words, the intensities of the bands from the primary probe with hybridized enhancement probes were greater than the band from the primary probe only. This showed that there were greater amounts of oligonucleotide in the denaturant, resulted from the hybridization of the enhancement probes to the primary probe in the first and the second hybridization mixtures.

Further experiments were performed under similar experiment conditions, except that the annealing buffer was changed to 2.5 M guanidinium thiocyanate. At this concentration, guanidinium thiocyante creates favorable hybridization conditions, therefore functions as an annealing solution. The hybridization reaction mixtures for these experiments were allowed to anneal at room temperature for 2 to 5 minutes. The method of analyzing the hybridization reaction results were the same as described above. Again, similar results were obtained as those using a 10× annealing buffer described above. More specifically, the intensities of the bands from either T- or L-primary probe with hybridized enhancement probes were greater than the band from the primary probe only. It is noted that the hybridization using guanidinium thiocyanate is more preferred because it allows for substantially shorter hybridization time at ambient temperature.

In the second method, AE-labeled enhancement probes were used. Each reaction involved two hybridization steps, as shown in FIG. 6.

In the first step, the hybridization mixture contained a capture oligonucleotide bound to agarose beads, a T- or L-primary probe and a hybridization buffer was incubated. Table 3 below shows the different combinations of hybridization buffers used in the two steps. After the first incubation step, the agarose beads were washed 3 times with 1 mL of 10 mM Tris solution and once with 50 µL of a probe diluent solution (0.1M sodium acetate, pH 5.0 with 0.1% SDS) to remove unhybridized primary probe.

In the second hybridization step, the washed agarose beads were mixed with a pair of AE-labeled enhancement probes and a hybridization buffer followed by an incubation.

TABLE 3

Hybridization Conditions

| Condition | Hybridization Step 1 | Hybridization Step 2 |
|---|---|---|
| 1 | 10X annealing buffer 60° C., at least 45 minutes | lithium succinate buffer* 60° C., at least 45 minutes |
| 2 | 1.8-2.0M guanidinium thiocyanate room temperature, at least 10 minutes | Lithium succinate buffer 60° C., at least 45 minutes |
| 3 | 1.8-2.0M guanidinium thiocyanate, room temperature, at least 10 minutes | 1.8-2.0M guanidinium thiocyanate room temperature, at least 10 minutes |

*0.1M lithium succinate buffer: 125 mM lithium hydroxide, 95 mM succinic acid, 1.5 mM EDTA, 1.5 mM EGTA, 8.5% lithium lauryl sulfate.

After the incubation was completed, the hybridization mixtures were centrifuged to "pellet" the agarose beads, and all but 50 µL of the supernatant was discarded. The 50 µL of the supernatant was set aside in a microcentrifuge tube for detection. The agarose beads were then washed 3 times with the probe diluent solution, with 50 µL of the first and third wash also being kept for detection. The presence of the AE-labeled probe was detected after injection of a triggering solution onto the agarose beads. The triggering solution activated instantaneously the acridinium ester labels on the enhancement probes that were captured on the agarose beads by hybridization and a "flash" type light emission was given off. The intensity of the flash could be observed by eye. The samples detected in these experiments included the washed agarose beads and aliquots from the supernatant of the hybridization mixture, and the first and third washes. To determine whether hybridization of the primary probe to the capture oligonucleotide and the hybridization of the AE-labeled enhancement probe to the primary probe occurred, the intensity of the light emission was observed.

Experiments were performed using different T- and L-primary probes with AE-labeled enhancement probes. It is noted that the first hybridization step were the same for the T- or L-primary probe used. The second hybridization step varied in that the first hybridization mixture contained only the AE-labeled enhancement probe that would hybridize to the enhancer linker segment of the primary probe. While the second hybridization mixture contained one pair of AE-labeled enhancement probes. Results from these tests using various T- and L-primary probes showed that there was a substantial increase in light emission when a pair of AE-labeled enhancement probes were used. This showed effective hybridization of the enhancement probes to the enhancer linker segment on the T- or L-primary probe and effective hybridization between the pair of the enhancement probes, which resulted in signal amplification.

EXAMPLE 5

Signal Amplification Using T- or L-Primary Probe with AE-Labeled Enhancement Probes This example describes the process of detection by a luminometer for signal amplification using the T- or L-primary probe with AE-labeled enhancement probes.

Materials and Methods

A polypropylene column was used as the assay vessel. The column was cylindrical with a filter (Porex (polyethylene, 0.35 micron thickness, 35 micron porosity)) placed at the bottom of the column. The capture support was placed on top of the filter, and retained inside the column by the filter disk during the reactions. The hybridization reactions occur inside the column while reaction mixtures and wash solutions flowing through the column driven by gravity. The liquid flowing out the column was collected by a test tube below the column.

The capture support was prepared as described in Example 1. Herein, the capture oligonucleotide contained a sequence complementary to the capture-binding segment of the target sequence of interest.

Measurement of the signal was performed using the TD 20/20 Luminometer (Turner Designs, Sunnyvale, Calif.). During the measurement, the column was placed in a 12 mm test tube holder in the sample chamber. At the bottom of the chamber was a collection vessel, for collecting the triggering solutions as they were added for detection. The collection vessel was made of a clear polypropylene material, which insured the light detection at the bottom of the sample chamber.

The triggering solution is a hydrogen peroxide solution. Acridinium ester reacts instantaneously (about 1 to 5 seconds) with hydrogen peroxide under alkaline condition to produce a light signal at 430 nm. The signal was measured continuously on the luminometer using the data stream feature, which provides real-time data collection. The data was collected at a rate of 5 readings per second.

Hybridization and Signal Measurement

There were three hybridization steps. In the first step, 50 µL of the capture support was placed in the column. The capture support contained a 27 base biotin labeled capture sequence immobilized onto streptavidin agarose beads. A target hybridization mixture containing a 100 base synthetic target oligonucleotide (20 µL of a concentration of 1 µg/µL), 1.8 M guanidinium thiocyanate (EDM Chemicals Inc., Gibbstown, N.J.), and 300 µL deionized water was placed in a 1.7 ml microcentrifuge tube. The target hybridization mixture was briefly vortexed, added into the column, and allowed to completely run through the column via gravitational flow. An additional 500 µl of 1.8 M guanidinium thiocyanate was then added into the column, and allowed to completely flow through. The capture support was then washed once with 1 mL 2×SSC buffer (0.3 M sodium chloride, 0.03 M sodium citrate), followed by two washes with 1 M Tris buffer. This hybridization step involved annealing of the complementary 27 base capture-binding segment of the synthetic targets to the immobilized capture sequence.

In the second step, the T-primary probe hybridization mixture was prepared next. In a 1.7 ml microcentrifuge tube, 20 µL T-primary probe (25 ng/µL), 180 µL of 5 M guanidinium thiocyanate (1.8 M final concentration) and 300 µL deionized water were combined. The T-primary probe hybridization mixture was briefly vortexed, added into the column, and allowed to completely run through the column via gravitational flow. An additional 500 µL of 1.8 M guanidinium thiocyanate was then added to the column, and allowed to completely flow through. The capture support was then washed once with 1 mL 2×SSC buffer, followed by two washes with 1 mL of 1 M Tris buffer. This step involved the hybridization of a 20 base target-binding segment of the T-primary probe to the complementary probe-binding segment of the synthetic target. This probe-binding segment does not overlap with the 27 base capture-binding segment of the synthetic target.

In the final hybridization step, a pre-enhancement probe hybridization buffer was first prepared. In a 1.7 mL microcentrifuge tube, 100 µg of sheared salmon sperm DNA (ss-DNA) (Eppendorf Scientific Inc., Westbury, N.Y.) was mixed with 1 mL of 2×SSC. The mixture was vortexed briefly and added into the column, and allowed to flow through the column completely. At the same time, the final enhancement probe hybridization mixture was prepared. In a 1.7 mL microcentrifuge tube, 20 µL AE-labeled enhancement probe 1C (0.1 µg/µL, shown in Table 1), 20 µL AE-labeled enhancement probe 1D (0.1 µg/µL, shown in Table 1), 180 µL of 5 M guanidinium thiocyanate (1.8 M final concentration) and 280 µL deionized water were combined. The enhancement probe hybridization mixture was briefly vortexed, added into the column, and allowed to flow through the column completely via gravitational flow. The capture support was then washed once with 1 mL of 2×SSC (37° C.), and followed by two washes with 1 mL of an AE-probe wash buffer (10 mM Tris-HCl, 10 mM EDTA, 2M NaCl, 0.01% Tween-20 at 37° C.) and three washes with 1 mL of 1 M Tris buffer (37° C.).

Immediately after the final wash completed flowing through the column, the detection of chemiluminescent signal was performed on the luminometer. The column was placed in the sample chamber and data collection was started. 100 µL of a first triggering solution of 0.1% hydrogen peroxide with 1 mM nitric acid was injected using a syringe. Then, 100 µL of a final triggering solution of 1 M NaOH was injected using another syringe. The real-time data was collected continuously during the addition of the triggering solutions. The collected data was post analyzed and could be displayed as a histogram of signal intensity vs. time.

In this example, a blank sample of deionized water was also prepared following all steps described above. Furthermore, an AE-labeled linear probe having 65 base synthetic oligonucleotides was used as a comparator of T- or L-primary probe of the present invention. It should be understood that using AE-labeled linear probe the hybridization reaction only involved the hybridization of AE-labeled linear probe to the target sequence captured on the capture support. In this situation, no complementary sequence segment was available for annealing of enhancement probe on to the linear probe.

FIGS. 7a and 7b show the measurement results in a bar graph of relative light units vs. concentrations of the target sequence, wherein the latter is also commonly referred to as copies of the target. As shown in FIG. 7a, using the AE-labeled linear probe at the concentration of the target sequence of $10^3$ copies, the signal was at the same level of that of the blank sample, which was the level of the background noise of the method. It is apparent that the detection limit using the AE-labeled linear probe was at $10^5$ copies of the target. Below this concentration, the result is unreliable since signal level falls within the error range of the background.

On the other hand, FIG. 7b shows significantly increased signal level using T-primary probe and enhancement probes of the present invention. More specifically, with $10^3$ copies of the target the signal level was substantially higher than the background. As shown, even with only 10 copies of the target the signal level was higher than the background taking account of the error range of the background.

The invention has been described with reference to particularly preferred embodiments. It will be appreciated, however, that various changes can be made without departing from the spirit of the invention, and such changes are intended to fall within the scope of the appended claims. While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method of enhancing detection signal for measurement of nucleic acid sequences comprising the steps of:
   (a) providing a solid capture support comprising an immobilized capture sequence complementary to a capture-binding segment of a single strand nucleic acid target sequence of interest;
   (b) hybridizing said capture-binding segment of said target sequence from a sample with said capture support to form a target-capture complex;
   (c) removing unhybridized target sequence;
   (d) providing a T- or L-primary probe comprising a target-binding segment and an enhancer linker segment; and hybridizing said target-binding segment of said primary probe with a probe-binding segment of said target sequence to form a capture-target-primary probe complex;
   (e) removing unhybridized T- or L-primary probe;
   (f) providing a first enhancement probe comprising a first annealing segment complementary to said enhancer linker segment of said primary probe, a second annealing segment and a chemical label; and hybridizing said first annealing segment of said first enhancement probe with said enhancer linker segment of said primary probe;
   (g) providing a second enhancement probe comprising a first annealing segment complementary to said second annealing segment of said first enhancement probe, a second annealing segment complementary to said first annealing segment of said first enhancement probe, and said chemical label, wherein each of said first and said second enhancement probes consists of a single molecule; and hybridizing said second enhancement probe with said first enhancement probe, thereby multiple said first and second enhancement probes annealing with each other in a pattern that said first annealing segment of said second enhancement probe anneals with said second annealing segment of said first enhancement probe, said first annealing segment of said first enhancement probe anneals with said second anneal segment of said second enhancement probe, thereby linking multiple said first and second enhancement probes alternately into a staggered chain extending from said enhancer linker segment of said primary probe, and forming a final complex containing multiple said chemical labels;
   (h) removing unhybridized said first and second enhancement probes;
   (i) detecting said chemical labels in said final complex; and
   (j) determining the presence of said target sequence in said sample.

2. The method of claim 1, wherein said chemical label is a chemiluminescence or a fluorescence molecule.

3. The method of claim 2 further comprising triggering chemical labels using a triggering solution prior to detecting said chemical labels in step (i).

4. The method of claim 1, wherein said removing unhybridized target sequence in step (c), said removing unhybridized T- or L-primary probe in step (e) and said removing unhybridized said first and second enhancement probes in step (h) are obtained by centrifugation and washing.

5. The method of claim 1, wherein said hybridizing to form said complexes in steps (d), (f) and (g) is performed using a guanidinium thiocyanate annealing solution.

6. The method of claim 1, wherein said primary probe is a T-primary probe having an asymmetric doubler phosphoramidite connecting between said target-binding segment and said enhancer linker segment.

7. The method of claim 1, wherein said primary probe is a L-primary probe having a spacer between said target-binding segment and said enhancer linker segment.

8. The method of claim 1, wherein said enhancer linker segment of said primary probe does not hybridize to said target sequence.

9. The method of claim 8, wherein said enhancer linker segment of said primary probe is the same as said second annealing segment of said second enhancement probe.

* * * * *

SEQUENCE LISTING

<160> NUMBER OF SEQ ID NOS: 25

<210> SEQ ID NO 1
<211> LENGTH: 22
<212> TYPE: DNA
<213> ORGANISM: Artificial Sequence
<220> FEATURE:
<223> OTHER INFORMATION: Probe

<400> SEQUENCE: 1
acttgcgtcg gcctagccgg ct                                            22

<210> SEQ ID NO 2
<211> LENGTH: 8
<212> TYPE: DNA
<213> ORGANISM: Artificial Sequence
<220> FEATURE:
<223> OTHER INFORMATION: Probe

<400> SEQUENCE: 2 atatatta                                                             8

<210> SEQ ID NO 3
<211> LENGTH: 27
<212> TYPE: DNA
<213> ORGANISM: Artificial Sequence
<220> FEATURE:
<223> OTHER INFORMATION: Probe

<400> SEQUENCE: 3
tcaggcgacg gctgaatcgg aaaggcc                                       27

<210> SEQ ID NO 4
<211> LENGTH: 22
<212> TYPE: DNA
<213> ORGANISM: Artificial Sequence
<220> FEATURE:
<223> OTHER INFORMATION: Probe

<400> SEQUENCE: 4
agccggctag gccgacgcaa gt                                            22

<210> SEQ ID NO 5
<211> LENGTH: 8
<212> TYPE: DNA
<213> ORGANISM: Artificial Sequence
<220> FEATURE:
<223> OTHER INFORMATION: Probe

<400> SEQUENCE: 5 tccctacg                                                             8

<210> SEQ ID NO 6
<211> LENGTH: 27
<212> TYPE: DNA
<213> ORGANISM: Artificial Sequence
<220> FEATURE:

<223> OTHER INFORMATION: Probe

<400> SEQUENCE: 6
ggcctttccg attcagccgt cgcctga                               27

<210> SEQ ID NO 7
<211> LENGTH: 19
<212> TYPE: DNA
<213> ORGANISM: Artificial Sequence
<220> FEATURE:
<223> OTHER INFORMATION: Probe

<400> SEQUENCE: 7
tgcgtcggcc tagccggct                                        19

<210> SEQ ID NO 8
<211> LENGTH: 24
<212> TYPE: DNA
<213> ORGANISM: Artificial Sequence
<220> FEATURE:
<223> OTHER INFORMATION: Probe

<400> SEQUENCE: 8
tcaggcgacg gctgaatcgg aaag                                  24

<210> SEQ ID NO 9
<211> LENGTH: 19
<212> TYPE: DNA
<213> ORGANISM: Artificial Sequence
<220> FEATURE:
<223> OTHER INFORMATION: Probe

<400> SEQUENCE: 9
agccggctag gccgacgca                                        19

<210> SEQ ID NO 10
<211> LENGTH: 23
<212> TYPE: DNA
<213> ORGANISM: Artificial Sequence
<220> FEATURE:
<223> OTHER INFORMATION: Probe

<400> SEQUENCE: 10
ctttccgatt cagccgtcgc tga                                   23

<210> SEQ ID NO 11
<211> LENGTH: 16
<212> TYPE: DNA
<213> ORGANISM: Artificial Sequence
<220> FEATURE:
<223> OTHER INFORMATION: Probe

<400> SEQUENCE: 11
gtcggcctag ccggct                                           16

<210> SEQ ID NO 12
<211> LENGTH: 15
<212> TYPE: DNA
<213> ORGANISM: Artificial Sequence
<220> FEATURE:
<223> OTHER INFORMATION: Probe

<400> SEQUENCE: 12
tcaggcgacg gctga                                            15

```
<210> SEQ ID NO 13
<211> LENGTH: 16
<212> TYPE: DNA
<213> ORGANISM: Artificial Sequence
<220> FEATURE:
<223> OTHER INFORMATION: Probe

<400> SEQUENCE: 13
agccggctag gccgac                                                    16

<210> SEQ ID NO 14
<211> LENGTH: 15
<212> TYPE: DNA
<213> ORGANISM: Artificial Sequence
<220> FEATURE:
<223> OTHER INFORMATION: Probe

<400> SEQUENCE: 14
tcagccgtcg cctga                                                     15

<210> SEQ ID NO 15
<211> LENGTH: 10
<212> TYPE: DNA
<213> ORGANISM: Artificial Sequence
<220> FEATURE:
<223> OTHER INFORMATION: Probe

<400> SEQUENCE: 15
gagatctcct                                                           10

<210> SEQ ID NO 16
<211> LENGTH: 10
<212> TYPE: DNA
<213> ORGANISM: Artificial Sequence
<220> FEATURE:
<223> OTHER INFORMATION: Probe

<400> SEQUENCE: 16
cgacaccgcc                                                           10

<210> SEQ ID NO 17
<211> LENGTH: 16
<212> TYPE: DNA
<213> ORGANISM: Artificial Sequence
<220> FEATURE:
<223> OTHER INFORMATION: Probe

<400> SEQUENCE: 17
agccggctag gccgac                                                    16

<210> SEQ ID NO 18
<211> LENGTH: 15
<212> TYPE: DNA
<213> ORGANISM: Artificial Sequence
<220> FEATURE:
<223> OTHER INFORMATION: Probe

<400> SEQUENCE: 18
gagatctcct cgaca                                                     15

<210> SEQ ID NO 19
<211> LENGTH: 5
<212> TYPE: DNA
<213> ORGANISM: Artificial Sequence
<220> FEATURE:
<223> OTHER INFORMATION: Probe
```

```
<400> SEQUENCE: 19 ccgcc                                                              5

<210> SEQ ID NO 20
<211> LENGTH: 20
<212> TYPE: DNA
<213> ORGANISM: Artificial Sequence
<220> FEATURE:
<223> OTHER INFORMATION: Probe

<400> SEQUENCE: 20
gagatctcct cgacaccgcc                                             20

<210> SEQ ID NO 21
<211> LENGTH: 3
<212> TYPE: DNA
<213> ORGANISM: Artificial Sequence
<220> FEATURE:
<223> OTHER INFORMATION: Probe

<400> SEQUENCE: 21 tct                                                                3

<210> SEQ ID NO 22
<211> LENGTH: 41
<212> TYPE: DNA
<213> ORGANISM: Artificial Sequence
<220> FEATURE:
<223> OTHER INFORMATION: Probe

<400> SEQUENCE: 22
agccggctag gccgacggat tgagatctcc tcgacaccgc c                      41

<210> SEQ ID NO 23
<211> LENGTH: 51
<212> TYPE: DNA
<213> ORGANISM: Artificial Sequence
<220> FEATURE:
<223> OTHER INFORMATION: Probe

<400> SEQUENCE: 23
agccggctag gccgacggat tcctcgacac cgcccttaga gtctccggaa c           51

<210> SEQ ID NO 24
<211> LENGTH: 41
<212> TYPE: DNA
<213> ORGANISM: Artificial Sequence
<220> FEATURE:
<223> OTHER INFORMATION: Probe

<400> SEQUENCE: 24
agccggctag gccgacggat tgcccttaga gtctccggaa c                      41

<210> SEQ ID NO 25
<211> LENGTH: 33
<212> TYPE: DNA
<213> ORGANISM: Artificial Sequence
<220> FEATURE:
<223> OTHER INFORMATION: Probe

<400> SEQUENCE: 25
gtcggcctag ccggctattc aggcgacggc tga                              33
```